(12) United States Patent
Suzuki (10) Patent No.: US 11,918,415 B2
(45) Date of Patent: Mar. 5, 2024

(54) ULTRASOUND ENDOSCOPE

(71) Applicant: OLYMPUS CORPORATION, Tokyo (JP)

(72) Inventor: Norihisa Suzuki, Sagamihara (JP)

(73) Assignee: Olympus Corporation, Tokyo (JP)

( * ) Notice: Subject to any disclaimer, the term of this patent is extended or adjusted under 35 U.S.C. 154(b) by 281 days.

(21) Appl. No.: 17/471,671

(22) Filed: Sep. 10, 2021

(65) Prior Publication Data

US 2022/0087641 A1  Mar. 24, 2022

Related U.S. Application Data (60) Provisional application No. 63/080,059, filed on Sep. 18, 2020.

(51) Int. Cl.
| | |
|---|---|
| *A61B 8/12* | (2006.01) |
| *A61B 1/00* | (2006.01) |
| *A61B 1/005* | (2006.01) |
| *A61B 8/00* | (2006.01) |
| *A61B 90/70* | (2016.01) |

(52) U.S. Cl.
CPC ............ *A61B 8/12* (2013.01); *A61B 1/00082* (2013.01); *A61B 1/005* (2013.01); *A61B 8/445* (2013.01); *A61B 90/70* (2016.02); *A61B 2090/701* (2016.02)

(58) Field of Classification Search
CPC ....... A61B 8/12; A61B 1/00082; A61B 1/005; A61B 90/70; A61B 2090/701
See application file for complete search history.

(56) References Cited

U.S. PATENT DOCUMENTS

| 2017/0014099 A1* | 1/2017 | Morimoto ............ A61B 8/5207 |
| 2020/0000429 A1 | 1/2020 | Morimoto |

FOREIGN PATENT DOCUMENTS

| JP | 3437318 B2 | 8/2003 |
| JP | 2007-089811 A | 4/2007 |
| JP | 2015-156903 A | 9/2015 |
| JP | 6170240 B2 | 7/2017 |
| JP | 6170240 B2 | 8/2017 |
| JP | 2019-041884 A | 3/2019 |
| WO | 2014/010283 A1 | 1/2014 |
| WO | 2015/151968 A1 | 10/2015 |

OTHER PUBLICATIONS

Office Action dated Aug. 16, 2022, issued in corresponding Japanese Patent Application No. 2021-136259.

* cited by examiner

*Primary Examiner* — Jason M Ip (74) *Attorney, Agent, or Firm* — Morgan, Lewis & Bockius LLP (57) ABSTRACT

An ultrasound endoscope comprises an operation portion, an insertion portion coupled to the operation portion, a distal end portion coupled to the insertion portion and including a projecting portion and a distal end body portion, a balloon channel disposed inside the insertion portion and extending from the operation portion to the rigid distal end portion, and a balloon mounting portion between the projecting portion and the distal end body portion. The balloon channel includes a bending portion in the rigid distal end portion and a balloon outlet that is formed at the bending portion and connected to the balloon mounting portion. A cross section of the bending portion includes a first bending angle and a second bending angle, and the first bending angle is smaller than the second bending angle.

13 Claims, 9 Drawing Sheets

ULTRASOUND ENDOSCOPE

RELATED APPLICATION DATA

This application is based on and claims priority under 35 U.S.C. § 119 to U.S. Provisional Application No. 63/080,059, filed Sep. 18, 2020, the entire contents of which are incorporated herein by reference.

FIELD OF THE INVENTION

The present disclosure relates to an ultrasound endoscope, and more particularly to, a balloon-assisted ultrasound endoscope.

DESCRIPTION OF THE RELATED ART

Various balloon-assisted ultrasound endoscopes have been developed and are well known.

A conventional balloon-assisted ultrasound endoscope typically includes an operation portion and an insertion tube extending from the operation portion and inserted into a subject. The insertion tube includes an elongated flexible portion and a distal end rigid portion. The distal end rigid portion is formed with a distal end body portion and an ultrasound probe that is fixed on the distal end body portion. The ultrasound probe can be covered by a balloon made of an elastic material. A balloon mounting portion for mounting the balloon is formed between the distal end body portion and the ultrasound probe.

Inside the operating section and the inserting section, a balloon channel is provided as an independent channel. The balloon channel may function as a balloon aspiration conduit as well as a balloon irrigation conduit. The balloon channel has an opening in the balloon mounting portion on which the balloon is mounted. When the balloon is inflated by a fluid sent via the balloon channel into the balloon through the opening, ultrasound diagnosis can be performed such that an ultrasound wave is transmitted from the ultrasound probe after the swollen balloon is brought into contact with a body cavity wall of a subject.

After the ultrasound diagnosis, the balloon has to be removed from the ultrasound endoscope. There is a case where contamination (such as a body fluid or other material) of a subject is suctioned using the balloon channel (negative pressure) and remains inside the balloon channel or other adjacent places. Thus, it is necessary to clean the contamination adhered to the inner surface of the balloon channel by a cleaning brush inserted into the balloon channel from the operation portion However, in the related art, it is difficult to make the rigid distal end portion short and compact and as the same time to make an easy-to-clean balloon channel. In particular, when using a hard type cleaning brush that has a high performance of removing contamination clogging, the rigid distal end portion of the conventional endoscope has to be made longer in the longitudinal direction, because it is necessary to make the balloon channel oblique so that the cleaning brush can be easily moved in and out of the rigid distal end portion. On the other hand, if the rigid distal end portion is made shorter, the hard tip of the cleaning brush remains inside the balloon channel and thus it is difficult to observe the position of the cleaning brush. As a result, the maneuverability of operating the cleaning brush deteriorates.

SUMMARY OF THE INVENTION

Accordingly, the present disclosure is directed to an ultrasound endoscope that substantially obviates one or more of the issues due to limitations and disadvantages of related art endoscope.

An object of the present disclosure is to provide an ultrasound endoscope comprising an operation portion for operating the ultrasound endoscope, an insertion portion coupled to the operation portion and configured to be inserted into a subject to be examined, a distal end portion coupled to the insertion portion and including a distal end body portion and a projecting portion that is projected from the distal end body portion; a channel disposed inside the insertion portion and extending from the operation portion to the distal end portion. The channel includes a bending portion in the distal end portion and a channel outlet that is formed at the bending portion. A cross section of the bending portion includes a first bending angle and a second bending angle, and the first bending angle is smaller than the second bending angle, such that the channel outlet is widened outwardly.

Another object of the present disclosure is to provide a balloon-assisted ultrasound endoscope comprises an operation portion for operating the ultrasound endoscope, an insertion portion coupled to the operation portion and configured to be inserted into a subject to be examined, a distal end portion coupled to the insertion portion and including a distal end body portion and a projecting portion that is projected from the distal end body portion, a balloon channel disposed inside the insertion portion and extending from the operation portion to the distal end portion, and a balloon mounting portion between the projecting portion and the distal end body portion and configured to mount a balloon to cover the projecting portion. The balloon channel includes a bending portion in the distal end portion and a balloon outlet that is connect to the bending portion. A cross section of the bending portion includes a first bending angle and a second bending angle, and the first bending angle is smaller than the second bending angle, such that the balloon outlet is widened outwardly.

Still another object of the present disclosure an ultrasound endoscope comprises an operation portion for operating the ultrasound endoscope, an insertion portion coupled to the operation portion and configured to be inserted into a subject to be examined, a distal end portion coupled to the insertion portion and including a distal end body portion and a projecting portion that projects from the distal end body portion, a balloon channel disposed inside the insertion portion and extending from the operation portion to the rigid distal end portion, and a balloon groove between the projecting portion and the distal end body portion. The balloon channel includes a balloon opening, and the balloon opening includes a first part on the balloon groove and a second part on the protruding portion.

Additional features and advantages will be set forth in the description that follows, and in part will be apparent from the description, or may be learned by practice of the invention. The objectives and other advantages of the disclosed input device will be realized and attained by the structure particularly pointed out in the written description and claims thereof as well as the appended drawings.

BRIEF DESCRIPTION OF THE DRAWING

The following detailed description of preferred embodiments can be read in connection with the accompanying drawings in which like numerals designate like elements and in which.

DETAILED DESCRIPTION

Hereinafter, exemplary embodiments of the present invention will be described in detail with reference to accompanying drawings.

Figure 1:
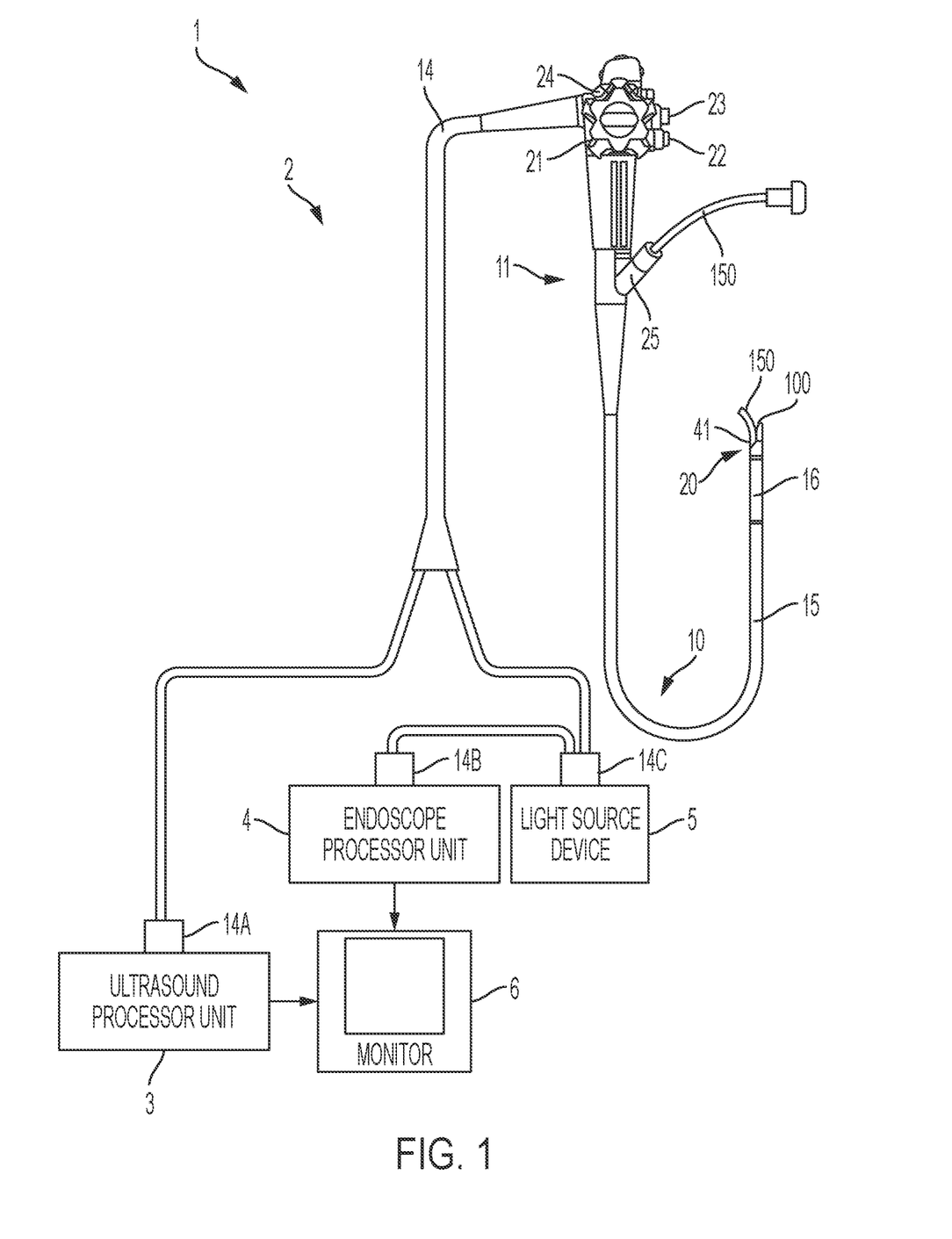
FIG. 1 is a general structural view of an ultrasound endoscope system including an exemplary ultrasound endoscope applicable to the present application.

FIG. 1 is a general structural view of an ultrasound endoscope system 1. The illustrated ultrasound endoscope system 1 includes an ultrasound endoscope 2 capable of taking an endoscope image and an ultrasound image of a region to be examined in the body, an ultrasound processor unit 3 that processes the ultrasound image, an endoscope processor unit 4 that processes the endoscope image, a light source device 5 that supplies illumination light to the ultrasound endoscope 2 to illuminate the region to be examined in the body, and a monitor 6 that displays the endoscope image and the ultrasound image.

The ultrasound endoscope 2 may be a convex type ultrasound endoscope, which includes an insertion tube 10 to be inserted into the body, the insertion tube 10 having a distal end and a base end, an operation portion 11 (by which an operator, such as a medical professional, operates the ultrasound endoscope 2) provided at the base end of the insertion tube 10, and a universal cord 14 that is connected to the operation portion 11. The universal cord 14 may include a plurality of connectors 14A, 14B, and 14C, by which the ultrasound endoscope 2 is connected to the ultrasound processor unit 3, the endoscope processor unit 4, and the light source device 5, respectively.

The universal cord 14 may be an ultrasound cable that can be detachably connected to the ultrasound endoscope 2, and thus makes the ultrasound endoscope easy to handle, reprocess and store.

The ultrasound endoscope system 1 may include an universal endoscopic ultrasound center that may include at least one of the ultrasound processor unit 3, the endoscope processor unit 4, and the light source device 5. The universal endoscopic ultrasound center may bring clarity to the ultrasound procedures, supporting better detection and characterization of lesions, and provides compatibility with linear endoscopes and radial ultrasound miniature probes.

The insertion tube 10 may further include a flexible portion 15, a curvature portion 16, and a distal end portion 20, which are provided in order from the base end to the distal end of the insertion tube 10.

The flexible portion 5 may have flexibility to curve in any direction along an insertion route of the insertion tube 10. The curvature portion 16 may curve in any directions, such as up-and-down and right-and-left directions or combinations thereof, by operating an angle knob 21 of the operation portion 11.

First Embodiment

Figure 2A:
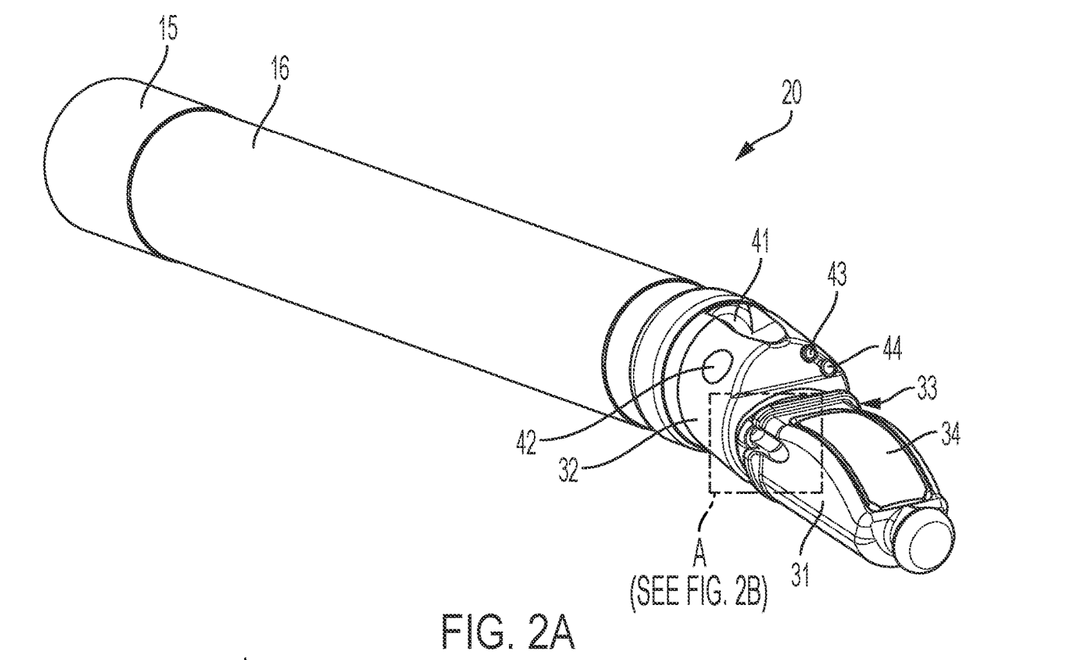
FIG. 2A is a perspective view illustrating a distal end portion of the ultrasound endoscope of FIG. 1 according to a first exemplary embodiment.

FIG. 2A is a perspective view illustrating the distal end portion 20 of the ultrasound endoscope 2 of FIG. 1 according to a first exemplary embodiment. As shown in FIG. 2A, the distal end portion 20 is extended from the curvature portion 16 and provided at the distal end of the insertion tube 10. In this exemplary embodiment, the distal end portion 20 is thin and rigid. For example, the distal end portion 20 may be formed of a rigid resin material or any other suitable materials. The rigid distal end portion 20 may include a projecting portion 31, a distal end body portion 32, and a balloon mounting portion 33 that is arranged between the projecting portion 31 and the distal end body portion 32.

Referring FIG. 2A, the projecting portion 31, which projects from the distal end body portion 32, may include a probe 34 such as an ultrasound transducer or the like. The distal end body portion 32 may include an instrument channel outlet 41, an ultrasound observation window 42, an objective lens 43, and a light guide lens 44.

The instrument channel outlet 41 is provided at a position on the distal end body portion 32 that is closer to the insertion tube 10 than the ultrasound observation window 42. The instrument channel outlet 41 allows an instrument tool 150 inserted into an instrument channel 45 (FIGS. 3A and 3B) in the insertion tube 10 from an instrument channel inlet 25 of the operation section 11 to be led outside the insertion section 10, generally during a procedure involving the ultrasound endoscope 2.

The distal end body portion 32 is arranged closest to the insertion tube 10 and optionally includes any further desired elements including, but not limited to, an objective lens, a light guide lens, an illumination window, an ultrasound observation window, and an air-and-water supply nozzle.

Figure 2B:
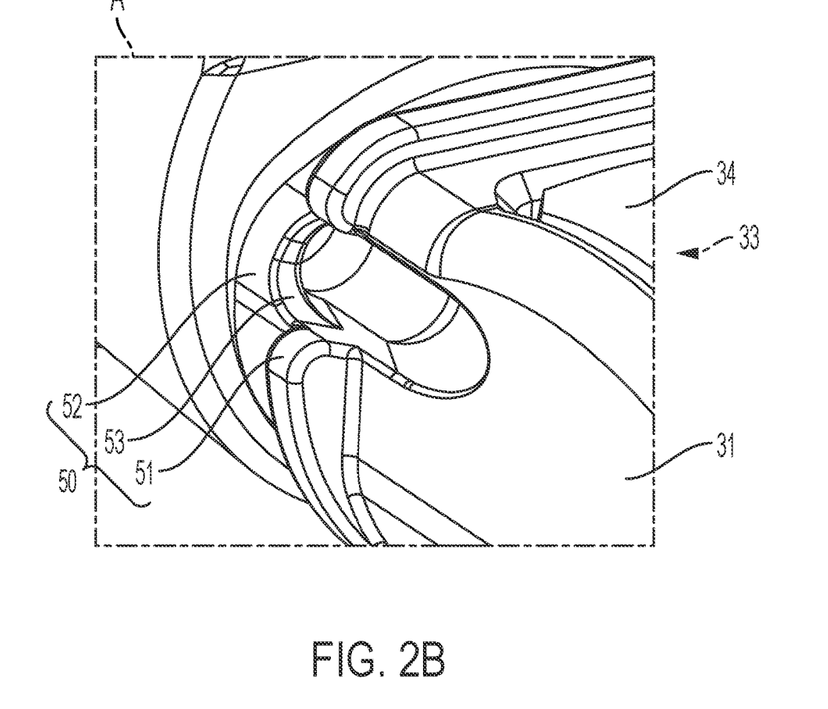
FIG. 2B is an enlarged perspective view illustrating region A of the rigid distal end portion of FIG. 2A.
Figure 2C:
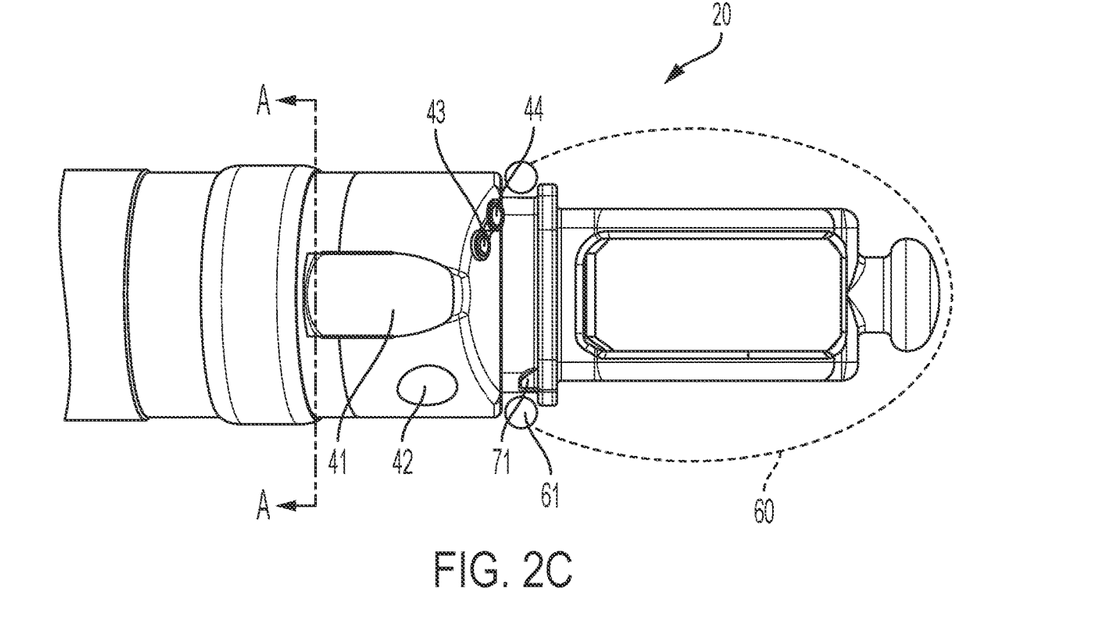
FIG. 2C is a top view of the rigid distal end portion of FIG. 2A.
Figure 2D:
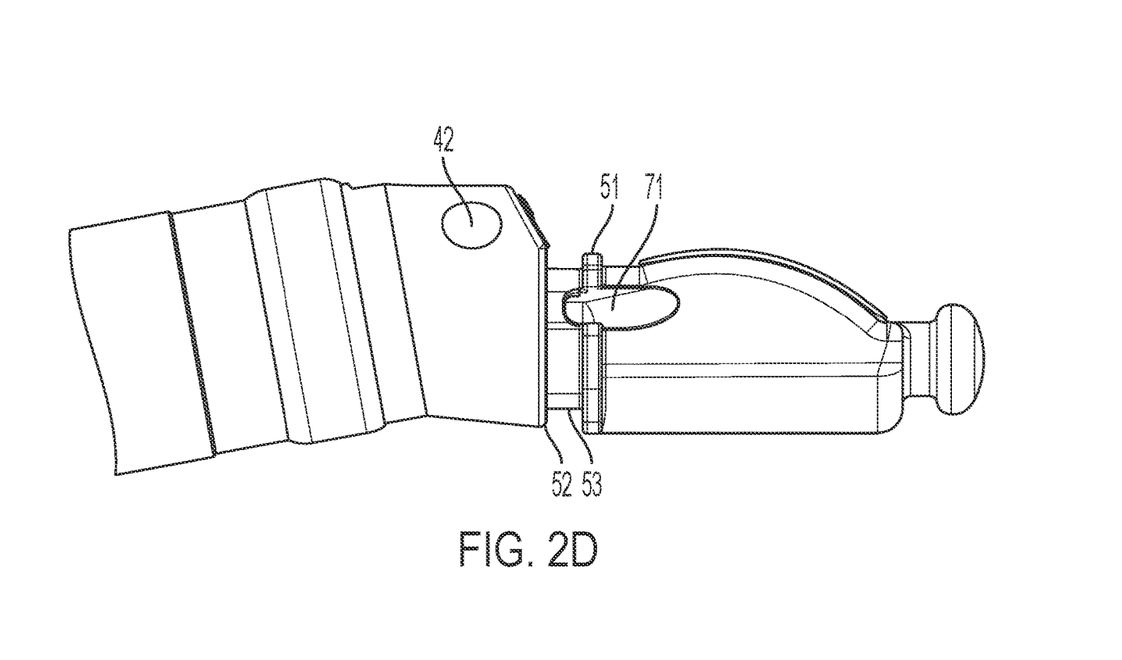
FIG. 2D is a side view of the rigid distal end portion of FIG. 2A.

FIG. 2B is an enlarged perspective view illustrating region A of the rigid distal end portion 20 of FIG. 2A, FIG. 2C is a top view of the rigid distal end portion 20 of FIG. 2A, and FIG. 2D is a side view of the rigid distal end portion 20 of FIG. 2A. As shown in FIG. 2B, the balloon mounting portion 33, in this exemplary embodiment, includes a balloon ring or groove 50. The balloon groove 50 may be formed with a first partition wall 51, a second partition wall 52, and a groove bottom portion 53 that is formed between the first partition wall 51 and the second partition wall 52. The first partition wall 51 separates the groove 50 from the projecting portion 31, and the second partition wall separates the groove 50 the distal end body portion.

The first partition wall 51 has a first outer diameter, and the second partition wall 52 has a second outer diameter. The first outer diameter of the first partition wall 51 is larger than the second outer diameter of the second partition wall 52. As shown in FIGS. 3B and 3C, the first partition wall 51 is higher than the second partition wall 52 in a cross-sectional view.

A balloon 60 can be detachably mounted on the balloon groove 50 by attaching a balloon band 61 on the groove bottom portion 53 between the first partition wall 51 and the second partition wall 52. In this exemplary embodiment, the distal end body portion 32 is a cylindrical body having an outer diameter that is larger than the respective first and second diameters of the first and second partition walls 51 and 52.

FIG. 2C shows a top view of FIG. 2A and FIG. 2D shows a side view of FIG. 2A, illustrating an exemplary structural arrangement of the projecting portion 31, the balloon mounting portion 33 and the distal end body portion 32. As shown in FIGS. 2C and 2D, the balloon mounting portion 33 includes the balloon groove 50, the balloon 60, and the balloon band 61 that surrounds the balloon groove 50.

Figure 3A:
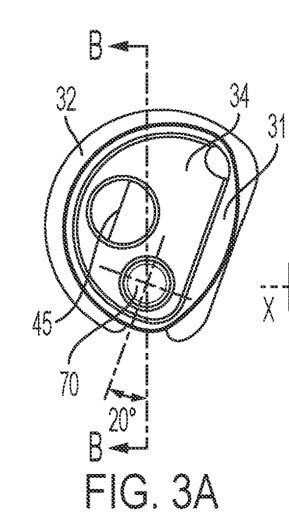
FIG. 3A is a sectional view observed from a direction of arrows A-A in FIG. 2C.
Figure 3B:
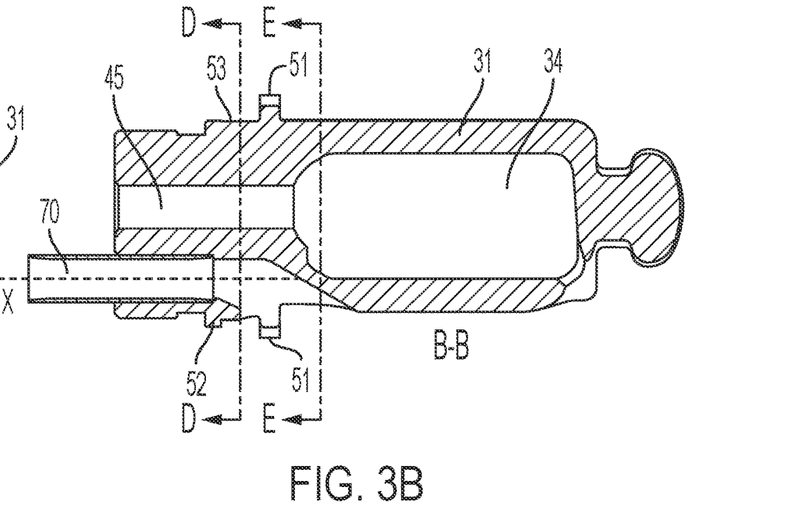
FIG. 3B is a first sectional view observed from a direction of arrows B-B in FIG. 3A.
Figure 3C:
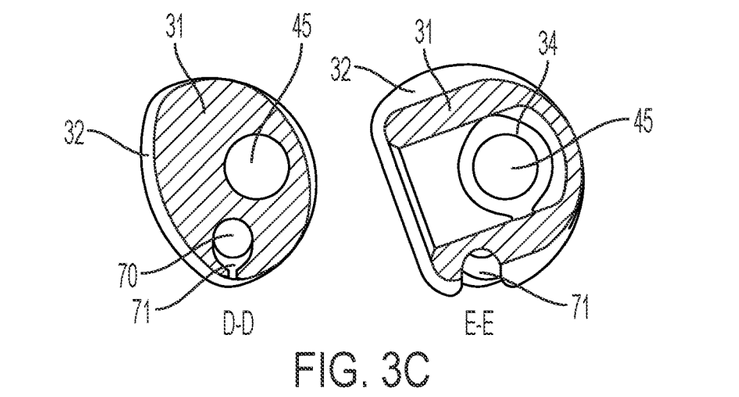
FIG. 3C are sectional views observed from directions of arrows D-D and E-E, respectively.
Figure 3D:
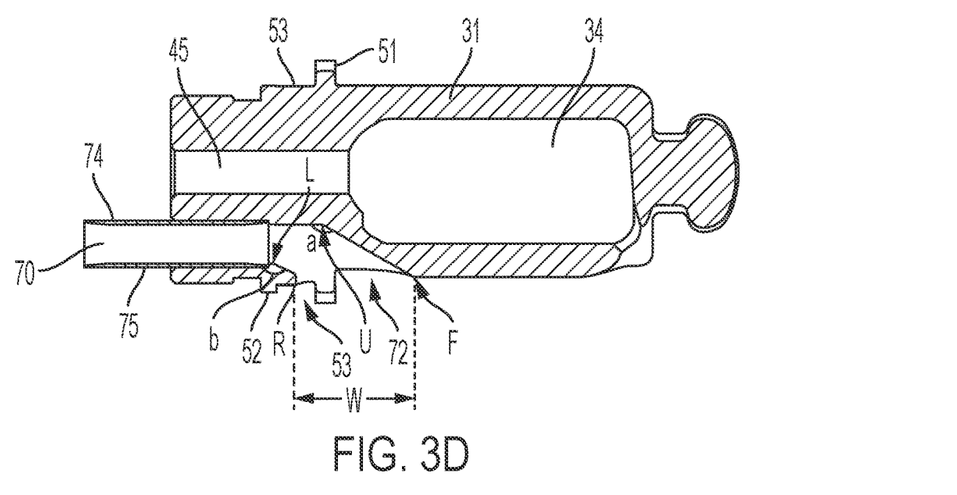
FIG. 3D is a second sectional view observed from a direction of arrows B-B in FIG. 3A.

FIG. 3A is a sectional view observed from a direction of arrows A-A in FIG. 2C, FIG. 3B is a sectional view observed at an angle of 20° from a direction of arrows B-B in FIG. 3A; FIG. 3C are sectional views observed from directions of arrows D-D and E-E, respectively; and FIG. 3D is also a sectional view observed from a direction of arrows B-B in FIG. 3A.

Inside the operating section 11 and the insertion section 10, as shown in FIGS. 3A and 3B, a balloon channel 70 may be provided at as an independent channel. The balloon channel 70 may function as a balloon aspiration conduit as well as a balloon irrigation conduit. The balloon channel 70 includes a balloon channel outlet or opening 71. The balloon channel outlet or opening 71 leads the balloon channel 70 at one edge side of the rigid distal end portion 20. When the balloon 60 is mounted on the balloon groove 50 by attaching the balloon band 61 on the groove bottom portion 53, the balloon channel outlet/opening 71 leads to an interior of the balloon 60 or is covered inside the balloon 60.

When the balloon 60 is inflated by a fluid sent via the balloon channel 70 through the balloon channel outlet/opening 7 ultrasound diagnosis can be performed by, for example, transmitting an ultrasound wave from the ultrasound transducer 34 after the swollen balloon is brought into contact with a body cavity wall of a subject.

After the ultrasound diagnosis is performed, the balloon 60 has to be removed from the ultrasound endoscope 2. There is a case where contamination (such as a body fluid or other material) of a subject is suctioned using the balloon channel 70 (negative pressure) and remains on the balloon channel 70 and adjacent places. Thus it is necessary to clean the contamination adhered to the inner surface of the balloon channel 70 and the projecting portion 31 by a cleaning brush 80 inserted into the balloon channel 70 from the operation portion 11.

Referring back to FIG. 2B, the balloon channel outlet/opening 71 is configured extending from the groove bottom portion 53 through the projecting portion 31. In this exemplary embodiment, as also shown in FIG. 3C, the balloon channel outlet/opening 71 is located at one edge side of the rigid distal end portion 20 including the projecting portion 31. The balloon channel outlet 71 is configured as an oval shape in this exemplary embodiment. However, the balloon channel outlet/opening 71 may be positioned at a different location and configured to be any other shapes that are suitable for the endoscopic operation and can contribute to a compact size of the rigid distal end portion the rigid distal end portion 20 of the insertion tube 10.

Also, as shown in FIG. 3D, the balloon channel outlet/opening 71 may include an opening rear end point R and an opening front end point F. A distance between the opening rear end point R and the opening front end point F represents a width W of a mouth 72 of the balloon channel opening 71 in a longitudinal direction of the balloon channel 70. The width W of the mouth 72 of the balloon channel opening 71 is designed to be suitable for the endoscopic operation and contributes to the compact size of the rigid distal end portion 20 of insertion tube 10.

Referring to FIG. 2B and FIG. 3D, the balloon channel opening 71 is formed by cutting off the groove bottom portion 53, the first partition wall 51 and the projecting portion 31, from the opening rear end point R through the opening front end F. Thus, the balloon channel outlet/opening 71 may include a first part formed on the groove bottom portion and a second part formed on the projecting portion 31. Thus, the mouth 72 of the balloon channel outlet/opening 71 may have a rear part and a front part that are defined by a virtual line of the cut-off first partition wall 51. The rear part of the mouth 72 has a width from the rear end point R to the virtual line of the cut-off first partition wall 51.

In this exemplary embodiment, as shown in FIG. 3D, the opening rear end point R is an initial cutting point for forming the balloon channel opening 71, and may be positioned at a center of the groove bottom portion 53. Thus, the width of the rear part of the mouth 72 is substantially a half of the width of the groove 50. Also, the rear part of the mouth 72 is substantially the same as the front part of the mouth 72 in size.

By forming part of the balloon channel opening 71 on the groove 50, a length of the projecting portion 31 of the distal end rigid portion can be made shorter. Also by forming the balloon channel opening 71 along the edge side of the projecting portion 31, the efficiency of utilizing the whole region of the projection portion 31 for accommodating the probe 34 and other necessary elements is improved. As a result, the rigid distal end portion of the insertion tube 10 can be made short and compact.

As shown in FIG. 3B, the balloon channel 70 is inclined away from its longitudinal direction X and extends to outside the rigid distal end portion 20 in an external radius direction of the rigid distal end portion 20. Thus, the balloon channel 70 includes a bending portion at which the balloon outlet/opening 71 is formed.

FIG. 3D also shows a cross sectional view of the bending portion of the balloon channel 70. As shown in FIG. 3D, the cross-section of the balloon channel 70 includes an upper balloon channel side 74 and a lower balloon channel side 75. The upper balloon channel side 74 includes a bending position U, and the lower channel side 75 includes a bending position L. The bending position U is closer to the projecting portion 31 than the bending position L. Also, the bending position U is approximately beneath the first partition wall 51, and the bending position L is approximately beneath the second partition wall 52.

Further, as shown in FIG. 3D, the bending position U may be defined by a bending angle "a" that is formed by the upper balloon channel side 74 and an oblique side connecting the bending position U and the opening front end point F. The lower bending position L may be defined by a bending angel "b" that is formed by the lower balloon channel side 75 and an oblique side connecting the bending position L and the opening rear end point R. Both the angle "a" and the angle "b" face outwardly. In this exemplary embodiment, the bending angle "b" is designed to be smaller than the bending angle "a". By such a structural arrangement, as illustrated in FIGS. 3B and 3D, an inner diameter of the balloon channel 70 becomes increasingly larger from the bending portion through the mouth 72 of the balloon channel outlet/opening 71.

Figure 4A:
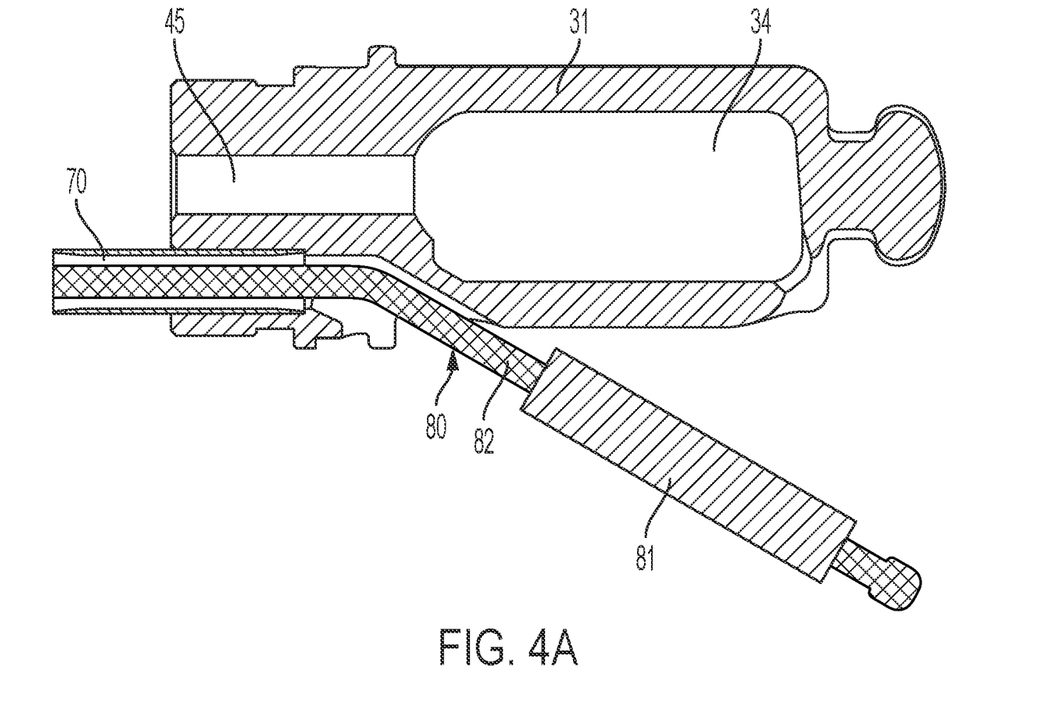
FIGS. 4A and 4B are each further sectional views observed from a direction of arrows B-B in FIG. 3A, in which a cleaning brush is moved out of the rigid distal end portion through a balloon channel outlet/opening according to the first exemplary embodiment (FIG. 4A) and in which the cleaning brush is moved in the rigid distal end portion through the balloon channel opening according to the first exemplary embodiment (FIG. 4B).
Figure 4B:
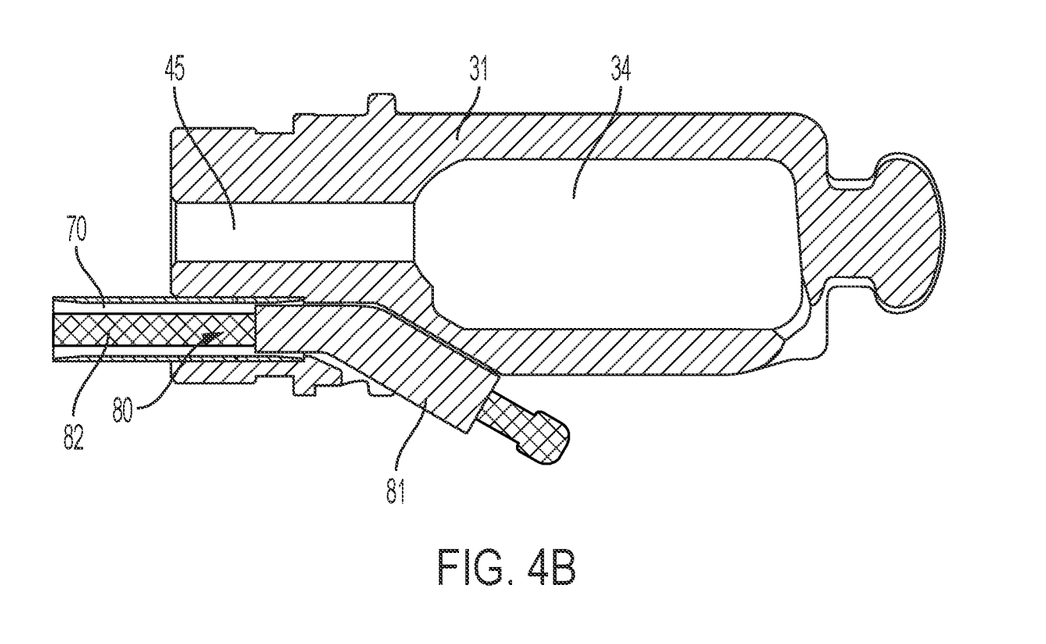

FIG. 4A is a sectional view observed from a direction of arrows B-B in FIG. 3A, in which a cleaning brush 80 is moved out of the rigid distal end portion 20 through the balloon channel outlet/opening 71 according to the first exemplary embodiment; and FIG. 4B is a sectional view observed from a direction of arrows B-B in FIG. 3A, in which the cleaning brush 80 is moved in the rigid distal end portion 20 through the balloon channel opening 71 according to the first exemplary embodiment.

As shown in FIGS. 4A and 4B, the cleaning brush 80 includes a hard tip 81 and a flexible body portion 82 connected to the hard tip 81. The cleaning brush 80 can be inserted from the tool inlet 25 (FIG. 1) into the balloon channel 70 to reach the balloon opening 71.

As described above, the bending angle "b" is defined smaller than the bending angle "a", the inner diameter of the balloon channel 70 increasingly gets larger toward the balloon channel outlet/opening 71, and the balloon channel outlet/opening 71 widens outwardly. By this structural arrangement, the cleaning brush 80 having the hard tip 81 is able to be easily moved in and out of the distal end rigid portion 20 including the projecting portion 31, and the length of the rigid distal end portion 20 can also be made shorter.

Second Embodiment

Figure 5A:
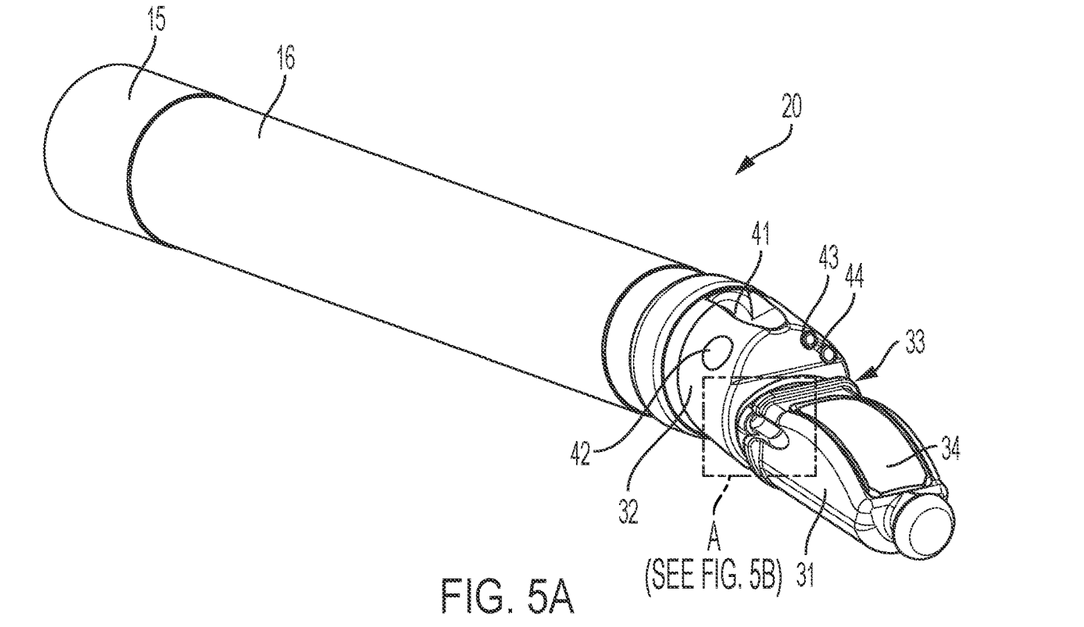
FIG. 5A is a perspective view illustrating a distal end portion of the ultrasound endoscope of FIG. 1 according to a second exemplary embodiment.

FIG. 5A is a perspective view illustrating the rigid distal end portion 20 of the ultrasound endoscope 2 of FIG. 1 according to a second exemplary embodiment. As shown in FIG. 5A, the rigid distal end portion 20 is extended from the curvature portion 16 and provided at the distal end of the insertion tube 10. In this exemplary embodiment, the rigid distal end portion 20 is thin and rigid. Thus, the rigid distal end portion 20 may be formed of a rigid resin material or any other suitable materials. The rigid distal end portion 20 may include a projecting portion 31, a distal end body portion 32, and a balloon mounting portion 33 that is arranged between the projecting portion 31 and the distal end body portion 32.

Referring FIG. 5A, the projecting portion 31 may include a probe 34 such as an ultrasound transducer or the like. The distal end body portion 32 may include an instrument channel outlet 41, an ultrasound observation window 42, an objective lens 43, and a light guide lens 44. The instrument channel outlet 41 is provided at a position on the distal end body portion 32 that is closer to the insertion tube 10 than the ultrasound observation window 42. The instrument channel outlet 41 allows an instrument tool 150 inserted into an instrument channel 45 (FIGS. 6A and 6B) in the insertion tube 10 from the tool inlet 25 of the operation section 11 to be led outside the insertion section 10, generally during a procedure involving the ultrasound endoscope 2.

The distal end body portion 32 is arranged closest to the insertion tube 10, and optionally may be provided with any further desired elements including, but not limited to, an objective lens, a light guide lens, an illumination window, an ultrasound observation window, and an air-and-water supply nozzle.

Figure 5B:
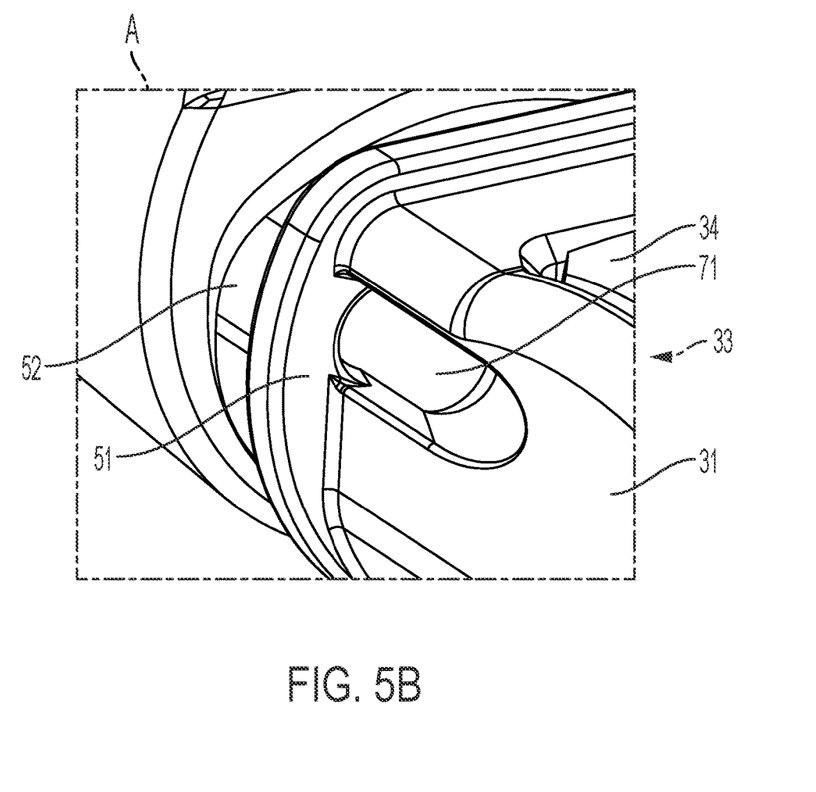
FIG. 5B is an enlarged perspective view illustrating region A of the rigid distal end portion of FIG. 5A.
Figure 5C:
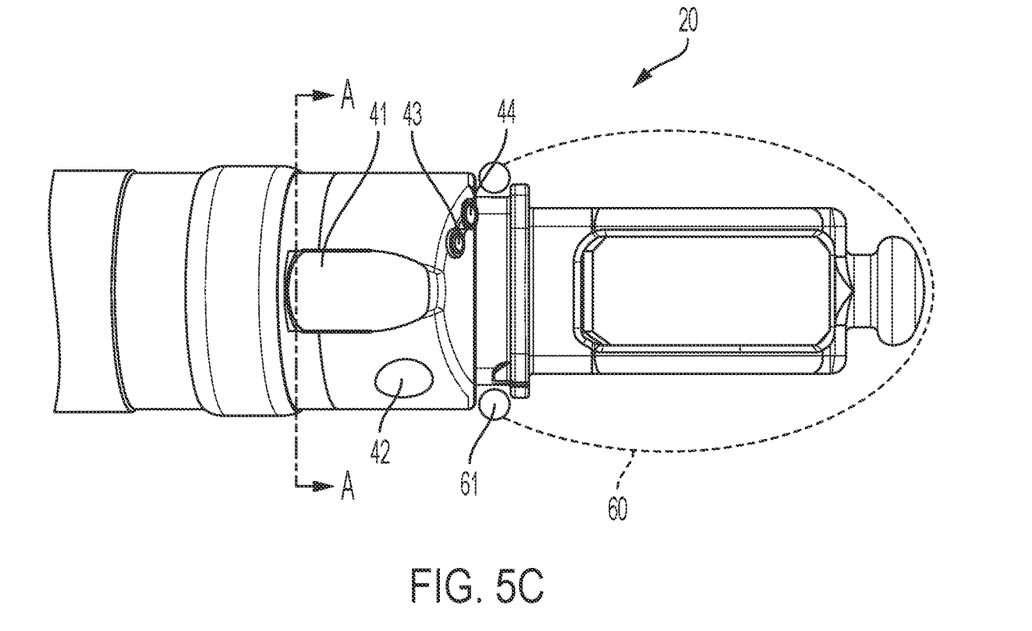
FIG. 5C is a top view of the rigid distal end portion of FIG. 5A.
Figure 5D:
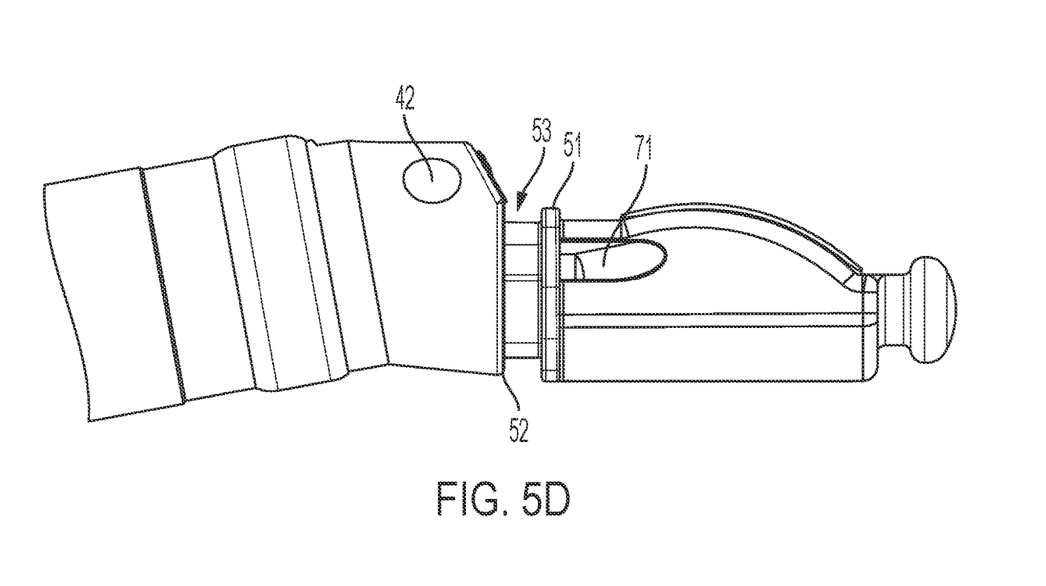
FIG. 5D is a side view of the rigid distal end portion of FIG. 5A.

FIG. 5B is an enlarged perspective view illustrating region A of the rigid distal end portion 20 of FIG. 5A, FIG. 5C is a top view of the rigid distal end portion 20 of FIG. 5A, and FIG. 5D is a side view of the rigid distal end portion 20 of FIG. 5A. As shown in FIGS. 5B-5D, the balloon mounting portion 33, in this exemplary embodiment, includes a balloon groove 50. The balloon groove 50 may be formed with a first partition wall 51, a second partition wall 52, and a groove bottom portion 53 that are formed between the first partition wall 51 and the second partition wall 52. The first partition wall 51 separates the groove 50 from the projecting portion 31. The second partition wall 52 separates the groove 50 from the distal end body portion 32.

A balloon 60 can be detachably mounted on the balloon groove 50 by attaching a balloon band 61 on the groove bottom portion 53 between the first partition wall 51 and the second partition wall 52. The first outer diameter of the first partition wall 51 is larger than the second outer diameter of the second partition wall 52. As shown in FIG. 6D, the first partition wall 51 is higher than the second partition wall 52 in a cross-sectional view.

Figure 6A:
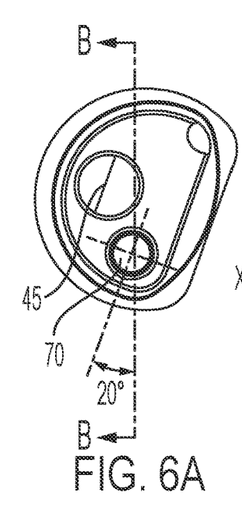
FIG. 6A is a sectional view observed from a direction of arrows A-A in FIG. 5C.
Figure 6B:
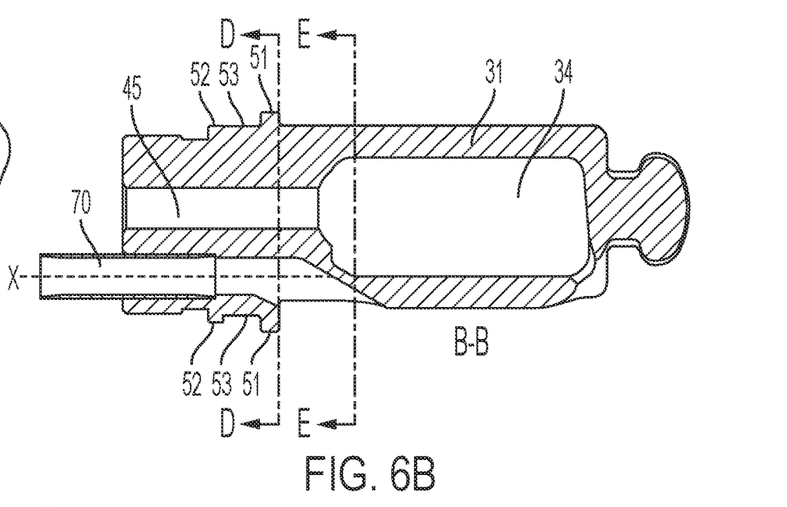
FIG. 6B is a first sectional view observed from a direction of arrows B-B in FIG. 6A.
Figure 6C:
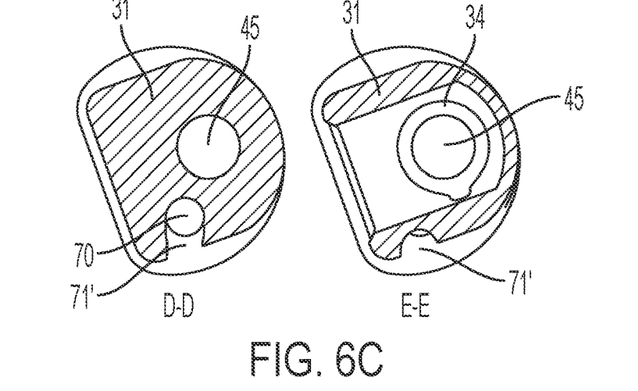
FIG. 6C are sectional views observed from directions of arrows D-D and E-E, respectively.
Figure 6D:
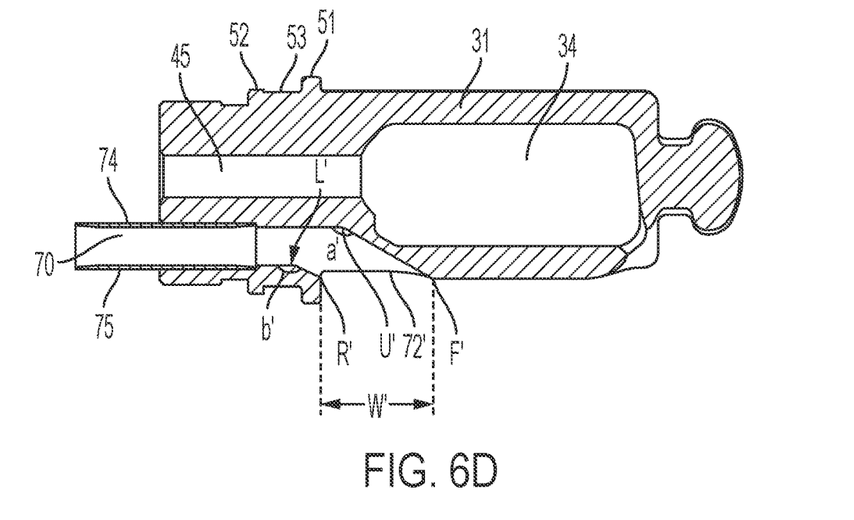
FIG. 6D is a second sectional view observed from a direction of arrows B-B in FIG. 6A.

FIG. 6A is a sectional view observed from a direction of arrows A-A in FIG. 5C, FIG. 6B is a first sectional view observed from a direction of arrows 13-B in FIG. 6A; FIG. 6C are sectional views observed from directions of arrows D-D and E-E, respectively; and FIG. 6D is also a second sectional view observed from a direction of arrows B-B in FIG. 6A.

Inside the operating section 11 and the insertion section 10, as shown in FIGS. 6A and 6B, a balloon channel 70 may be provided as an independent channel. The balloon channel 70 may function as a balloon aspiration conduit as well as a balloon irrigation conduit. The balloon channel 70 includes a balloon channel outlet/opening 71'. When the balloon 60 is mounted on the balloon groove 50 by attaching the balloon band 61 on the groove bottom portion 53, the balloon channel opening 71' is position and covered inside the balloon 60.

When the balloon 60 is inflated by a fluid sent via the balloon channel 70 through the balloon channel opening 71', ultrasound diagnosis can be performed such that an ultrasound wave is transmitted from the ultrasound transducer 34 after the swollen balloon is brought into contact with a body cavity wall of a subject.

After the ultrasound diagnosis is performed, the balloon 60 has to be removed from the ultrasound endoscope 2. There is a case where contamination (such as a body fluid or other material) of a subject is suctioned using the balloon channel 70 (negative pressure). Thus it is necessary to clean the contamination adhered to the inner surface of the balloon channel 70 and the projecting portion 31 by a cleaning brush 80 inserted into the balloon channel 70 from behind.

Unlike the first embodiment in which the balloon channel outlet/opening 71 includes a first part formed on the balloon groove 50 and the second part formed on the projecting portion 31, in this second embodiment, as shown in FIG. 5B, the balloon channel outlet/opening 71' is formed on the projecting portion 31 and extended from the first partition wall 51 through the projecting portion 31.

As shown in FIGS. 5B and 6A, the balloon channel outlet/opening 71' is located at one edge side of the projecting portion 31 of the distal end rigid portion 20. In this exemplary embodiment, the balloon channel outlet 71' is configured to be an oval shape. The balloon channel outlet/opening 71' may be positioned at a different location and configured to be any other shapes that are suitable for the medical operation and can contribute to a compact size of the rigid distal end portion 20 of the insertion tube 10.

As shown in FIGS. 6B and 6D, the balloon channel 70 is inclined crossing its longitudinal direction X and extends to outside the rigid distal end portion 20 in an external radius direction of the rigid distal end portion 20 including the projecting portion 31. Thus, the balloon channel 70 includes a bending/inclining portion at which the balloon outlet/opening 71' is formed.

FIG. 6D shows the bending portion of the balloon channel 70 in details. Specifically, as shown in FIG. 6D, the cross-section of the balloon channel 70 includes an upper balloon channel side 74 and a lower balloon channel side 75. The upper balloon channel side 74 includes a bending position and the lower channel side 75 includes a bending position U. The bending position U' is closer to the producing portion 31 than the bending position L'.

Also, as shown in FIG. 6D, the balloon channel opening 71' may include an opening rear end point R' and an opening front end point F'. A distance between the opening rear end point R' and the opening front end point F' represent a width W' of a mouth 72' of the balloon channel opening 71' in a longitudinal direction X of the balloon channel 70. The width W' of the balloon channel opening 71 is designed to be suitable for the medical operation including the cleaning operation and contributable for the compact size of the rigid distal end portion 20 of insertion tube 10.

Referring to FIG. 5B and FIG. 6D, the balloon channel opening 71' is formed on the projecting portion 31 by cutting off part of the projecting portion 31 from the opening rear end point R through the opening front end point F'. The balloon channel opening 71' extends from the first partition wall 51 along one edge side of the projecting portion 31. By forming the balloon channel opening 71' along the one edge side of the projecting portion 31, the efficiency of utilizing the whole region of the projection portion 31 for accommodating the probe 34 and other necessary elements is improved. As a result, the rigid distal end portion 20 can be made short and compact.

Also, as shown in FIG. 6D, the bending position is defined by a bending angle "a'" that is formed by the upper balloon channel side 74 and a first oblique side connecting the bending position U' and the opening front end point F'. The lower bending position L' is defined by a bending angel "b'" that is formed by the lower balloon channel side 75 and a second oblique side connecting the bending position L and the opening rear end point R'. Both the angle "a'" and the angle "b'" face outwardly. In this exemplary embodiment, the bending angle "b'" is designed to be smaller than the bending angle "a'". By such a structural arrangement, as illustrated in FIGS. 6B and 6D, an inner diameter of the balloon channel 70 becomes increasingly larger from the bending portion through the mouth 72' of the balloon channel outlet/opening 71'.

Figure 7A:
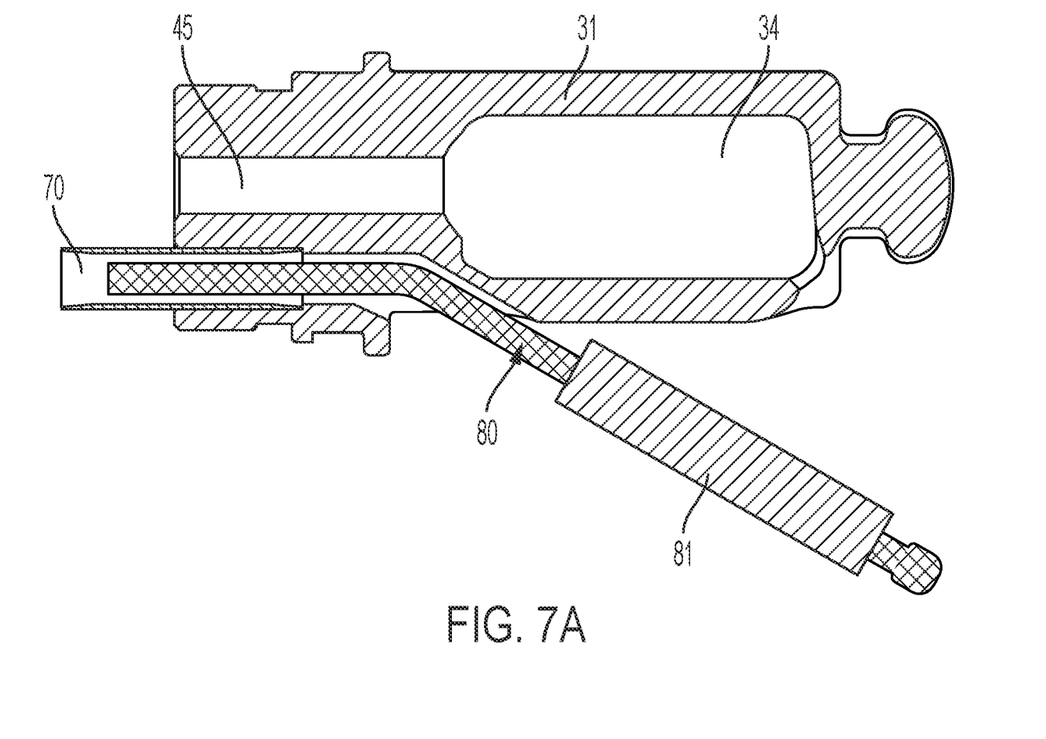
FIGS. 7A and 7B are each further sectional views observed from a direction of arrows B-B in FIG. 6A, in which a cleaning brush is moved out of the rigid distal end portion through a balloon channel outlet/opening according to the second exemplary embodiment (FIG. 7A) and in which the cleaning brush is moved in the rigid distal end portion through the balloon channel opening according to the second exemplary embodiment (FIG. 7B).
Figure 7B:
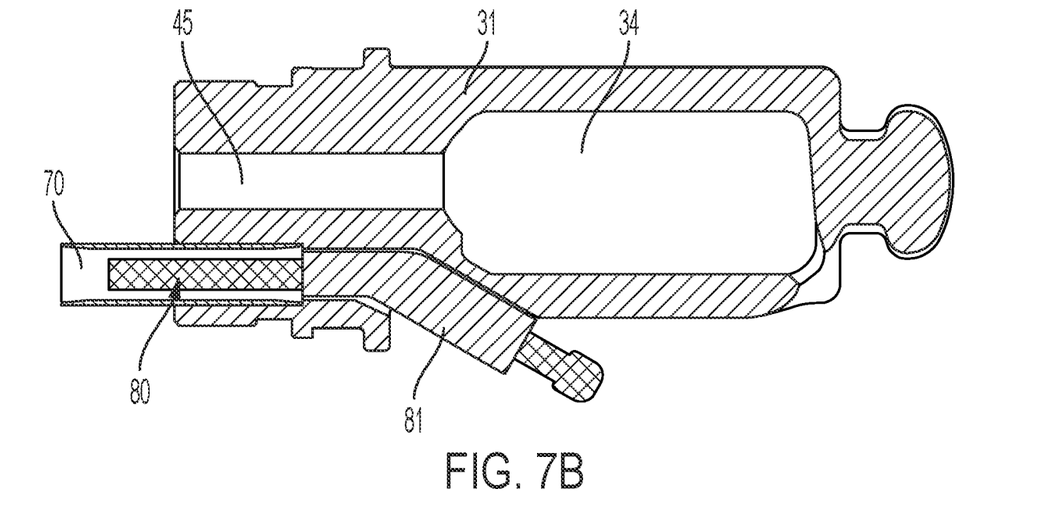

FIG. 7A is a sectional view observed from a direction of arrows B-B in FIG. 6A, in which a cleaning brush 80 is moved out of the rigid distal end portion 20 through the balloon channel outlet/opening 71' according to the second exemplary embodiment; and FIG. 7B is a sectional view observed from a direction of arrows B-B in FIG. 6A, in which the cleaning brush 80 is moved in the rigid distal end portion 20 through the balloon channel opening 71' according to the second exemplary embodiment.

As shown in FIGS. 7A and 7B, the cleaning brush 80 includes a hard tip 81 and a flexible body portion 82 connected to the hard tip 81. The cleaning brush 80 can be inserted from the tool inlet 25 (FIG. 1) into the balloon channel 70 to reach the balloon opening 71.

As described above, the bending angle "b'" is defined smaller than the bending angle "a'", the inner diameter of the balloon channel 70 increasingly gets larger toward the balloon channel outlet/opening 71', and the balloon channel outlet/opening 71' widens outwardly. By this structural arrangement, the cleaning brush 80 having the hard tip 81 is able to be easily moved in and out of the distal end rigid portion 20 including the projecting portion 31, and the length of the rigid distal end portion 20 can also be made shorter.

Although the present invention has been described in connection with the above exemplary embodiments, it will be appreciated by those skilled in the art that additions, deletions, modifications, and substitutions not specifically described may be made without department from the spirit and scope of the invention as defined in the appended claims.

What is claimed is:

1. A balloon-assisted ultrasound endoscope, comprising:
an operation portion for operating the ultrasound endoscope;
an insertion portion coupled to the operation portion and to be inserted into a subject to be examined;
a distal end portion coupled to the insertion portion and including a projecting portion and a distal end body portion;
a balloon channel disposed inside the insertion portion and extending from the operation portion to the distal end portion; and
a balloon mounting portion between the projecting portion and the distal end body portion and configured to mount a balloon to cover the projecting portion,
wherein the balloon channel includes a bending portion in the distal end portion, and a balloon channel outlet that is connected to the bending portion,
wherein a cross section of the bending portion includes a first bending angle and a second bending angle, and the first bending angle is smaller than the second bending angle, such that the balloon channel outlet is widened outwardly,
wherein the balloon mounting portion includes a groove,
wherein the groove includes a first partition wall, a second partition wall, and a groove bottom portion between the first partition wall and the second partition wall, where the first partition wall separates the groove bottom portion from the projecting portion and the second partition wall separates the bottom portion from the distal end body portion, and
wherein a mouth of the balloon channel outlet extends from a position distal of the first partition wall into the projecting portion.

2. The ultrasound endoscope according to claim 1, wherein a distal end of the mouth of the balloon channel outlet is located in the groove bottom portion.

3. The ultrasound endoscope according to claim 2, wherein the mouth of the balloon channel outlet includes a first part on the groove and a second part on the projecting portion.

4. The ultrasound endoscope according to claim 2, wherein the balloon channel outlet passes through the first partition wall, and includes a first part on the groove bottom portion and the first partition wall and a second part on the projecting portion.

5. The ultrasound endoscope according to claim 1, wherein the mouth of the balloon channel outlet is positioned at one edge side of the projecting portion.

6. The ultrasound endoscope according to claim 3, wherein a width of the first part of the balloon channel outlet in a longitudinal direction of the balloon channel is a half of a width of the groove.

7. The ultrasound endoscope according to claim 1, wherein the cross section of the bending portion of the balloon channel includes an upper side and a first oblique side that define the first bending angle;
wherein the cross section of the bending portion of the balloon channel includes a lower side and a second oblique side that define the second bending angle; and
wherein the second oblique side is inclined more outwardly than the first oblique side.

8. The ultrasound endoscope according to claim 1, wherein the mouth of the balloon channel outlet is inside the balloon when the balloon is mounted on the balloon mounting portion.

9. The ultrasound endoscope according to claim 1, wherein the balloon channel includes an inner diameter that becomes increasingly larger from the bending portion toward the mouth of the balloon channel outlet.

10. The ultrasound endoscope according to claim 1, wherein the first partition wall includes an outer diameter that is larger than that of the second partition wall, and the distal end body portion includes an outer diameter that is larger than the respective outer diameters of the first and second partition walls of the balloon groove.

11. The ultrasound endoscope according to claim 1, further comprising a cleaning brush, wherein the cleaning brush is configured to be insertable into the balloon channel and slidably movable through the balloon channel outlet.

12. The ultrasound endoscope according to claim 1, wherein the balloon is inflated and contracted by a fluid that is supplied to and discharged from the balloon channel.

13. The ultrasound endoscope according to claim 11, wherein the cleaning brush includes a flexible body portion connected to a tip.

* * * * *